(12) United States Patent
Desphande et al.

(10) Patent No.: US 7,244,842 B2
(45) Date of Patent: Jul. 17, 2007

(54) AMORPHOUS HYDRATE OF A CEPHALOSPORIN ANTIBIOTIC

(75) Inventors: Pandurang Balwant Desphande, Chennai (IN); Bhausaheb Pandharinath Khadangale, Chennai (IN); Chandrasekaran Ramasubbu, Chennai (IN)

(73) Assignee: Orchid Chemicals & Pharmaceuticals Ltd., Chennai (IN)

( * ) Notice: Subject to any disclaimer, the term of this patent is extended or adjusted under 35 U.S.C. 154(b) by 0 days.

(21) Appl. No.: 10/532,753

(22) PCT Filed: Nov. 10, 2003

(86) PCT No.: PCT/IB03/05032

§ 371 (c)(1),
(2), (4) Date: May 13, 2005

(87) PCT Pub. No.: WO2004/046154

PCT Pub. Date: Jun. 3, 2004

(65) Prior Publication Data

US 2006/0094703 A1 May 4, 2006

(30) Foreign Application Priority Data

Nov. 15, 2002 (IN) .................... 848/2002
Feb. 26, 2003 (IN) .................... 152/2003

(51) Int. Cl.
*C07D 501/22* (2006.01)

(52) U.S. Cl. .................................... 540/222

(58) Field of Classification Search ............... None
See application file for complete search history.

(56) References Cited

U.S. PATENT DOCUMENTS

| | | | | |
|---|---|---|---|---|
| 4,559,334 A | * | 12/1985 | Takaya et al. | 514/202 |
| 4,935,507 A | * | 6/1990 | Takaya et al. | 540/222 |
| 5,847,118 A | * | 12/1998 | Karimian et al. | 540/222 |
| 6,294,669 B1 | * | 9/2001 | Yasui et al. | 540/227 |
| 6,350,869 B1 | * | 2/2002 | Sturm et al. | 540/220 |
| 6,384,213 B1 | * | 5/2002 | Handa et al. | 540/222 |
| 6,878,827 B2 | * | 4/2005 | Ono et al. | 548/194 |
| 7,105,659 B2 | * | 9/2006 | Dandala et al. | 540/222 |
| 2005/0215781 A1 | * | 9/2005 | Chandrasekaran et al. | 540/222 |
| 2005/0245738 A1 | * | 11/2005 | Singh et al. | 540/222 |
| 2006/0025399 A1 | * | 2/2006 | Law et al. | 514/202 |
| 2006/0029674 A1 | * | 2/2006 | Sever et al. | 424/486 |
| 2006/0069079 A1 | * | 3/2006 | Sever et al. | 514/202 |
| 2006/0074236 A1 | * | 4/2006 | Pozzi et al. | 540/222 |
| 2006/0111566 A1 | * | 5/2006 | Pozzi et al. | 540/217 |
| 2006/0142261 A1 | * | 6/2006 | Law et al. | 514/202 |
| 2006/0142563 A1 | * | 6/2006 | Law et al. | 540/222 |
| 2006/0149056 A1 | * | 7/2006 | Singh et al. | 540/222 |
| 2006/0211676 A1 | * | 9/2006 | Law et al. | 514/200 |

FOREIGN PATENT DOCUMENTS

| | | | |
|---|---|---|---|
| WO | WO 1079211 A1 | * | 1/2001 |
| WO | WO 2006006040 A2 | * | 1/2006 |
| WO | WO 2006010978 A1 | * | 2/2006 |
| WO | WO 2006053625 A1 | * | 5/2006 |

OTHER PUBLICATIONS

Maritza González, II Farmaco, vol. 58, Issue 6, Jun. 2003, pp. 409-418.*

* cited by examiner

*Primary Examiner*—Mark L. Berch
(74) *Attorney, Agent, or Firm*—Oliff & Berridge PLC

(57) ABSTRACT

A process for the preparation of cefdinir of the formula (I) the said process comprising the steps of: i) condensing 7-amino-3-cephem-4-carboxylic acid of the formula (XII) wherein R1 is as defined above with compound of the formula (XIII) in the presence of a tertiary amine and an organic solvent, followed by treatment with a base to produce a salt of compound formula (XIV), wherein M+ is a counter ion and ii) hydrolyzing the compound of the formula (XIV) using an acid in the presence of a solvent to produce cefdinir of formula (I).

13 Claims, 1 Drawing Sheet

AMORPHOUS HYDRATE OF A CEPHALOSPORIN ANTIBIOTIC

FIELD OF THE INVENTION

The present invention relates to a novel amorphous hydrate of a cephalosporin antibiotic. More particularly, the present invention relates to novel amorphous monohydrate of cefdinir of the formula (I).

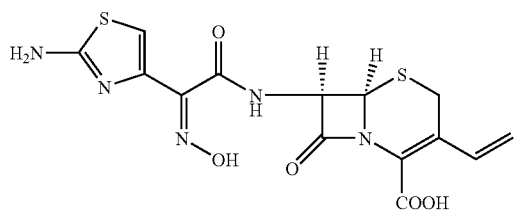

(I)

The present invention also provides a process for the preparation of the novel amorphous monohydrate of cefdinir of formula (I).

The present invention also provides new salts of compound of formula (XIV) and a process for the preparation of cefdinir using the new salts.

BACKGROUND OF THE INVENTION

Cefdinir is a third generation cephalosporin antibiotic for oral administration and has a broader antibacterial spectrum over the general gram positive and gram negative bacteria, especially against *Streptococci*, than other antibiotics for oral administration.

In view of the vital antibiotic activities of cefdinir of the formula (I), various methods of preparation were reported. Cefdinir is for the first time claimed in U.S. Pat. No. 4,559,334 and the nature of the product that is disclosed in this patent is described as crystalline like amorphous in subsequent US patent (U.S. Pat. No. 4,935,507). This patent also discloses a process for the preparation of cefdinir as depicted in the Scheme I.

In the disclosed process, 7-amino-3-vinyl-3-cephem-4-carboxylic acid ester where R represents a conventional carboxy protecting group, is acylated with the reactive ester of haloacylacetic acid, which was converted to its oxime, followed by cyclization with thiourea and deprotection of the ester group to afford cefdinir. The product obtained by the process described in examples 14 and 16 is approximately 80–85% pure. The cyclization step suffers from poor yield and affords brownish color of the thiazole derivative, which subsequently affords cefdinir, but quality and yield were inferior. Further, owing to the fact that the expensive 7-amino-3-vinyl-3-cephem-4-carboxylic acid is carried through four steps, cost of producing cefdinir is high.

U.S. Pat. No. 4,935,507 claims the novel crystalline form of the cefdinir syn-isomer and a process for preparing the same. The X-ray crystallography data given in this patent is given in the following table:

| 2 θ ° Values | Relative Intensity |
|---|---|
| 14.7 | 76 |
| 17.8 | 56 |
| 21.5 | 100 |
| 22.0 | 70 |
| 23.4 | 38 |
| 24.4 | 80 |
| 28.0 | 40 |

The crystalline form (Crystal A) of U.S. Pat. No. 4,935,507 is prepared from the syn-isomer prepared according to the procedures described in Examples 14 and 16 of U.S. Pat. No. 4,559,334.

In our U.S. Pat. No. 6,388,070, we disclosed a process for preparing a compound of formula (VIII), wherein, $R_1$ represents H, trityl, etc., $R_2$ represents H, phenyl, etc., $R_3$ represents $CH_3$, $CH=CH_2$, etc., $R_4$ is H or a salt or a carboxylic protecting group; $R_5$ is H or trimethylsilyl; comprising acylating the compound of formula (VI) with compound of formula (VII) in the presence of an organic solvent, Scheme I

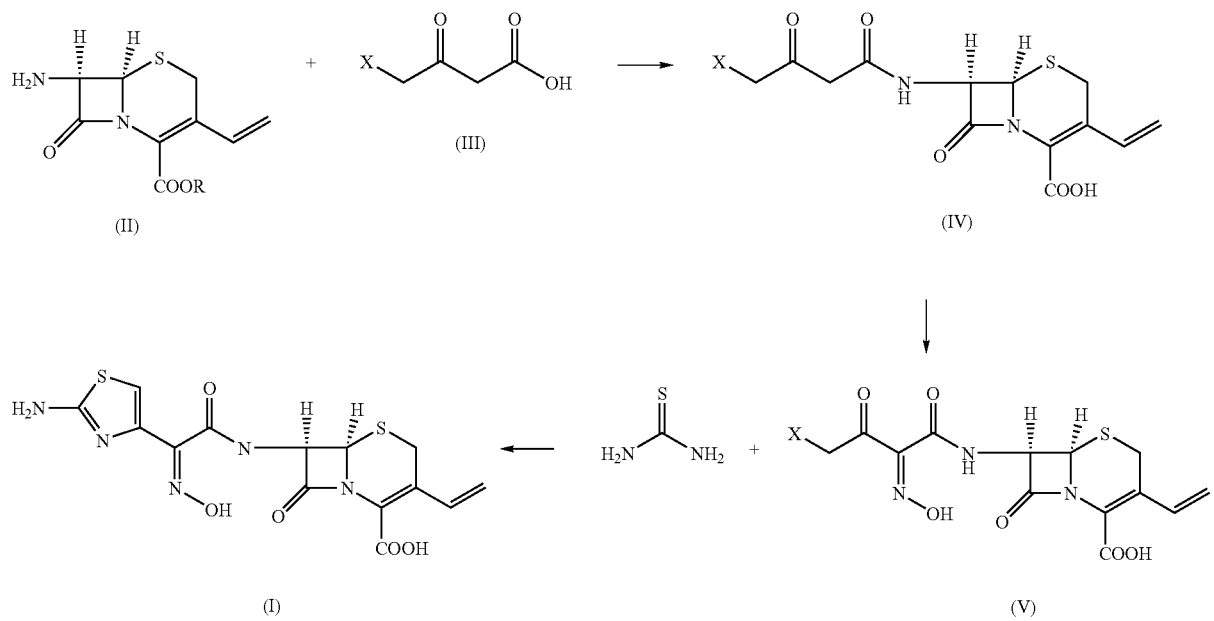

organic base and a silylating agent at a temperature in the range of −10° C. to +30° C. The reaction is shown in scheme II below:

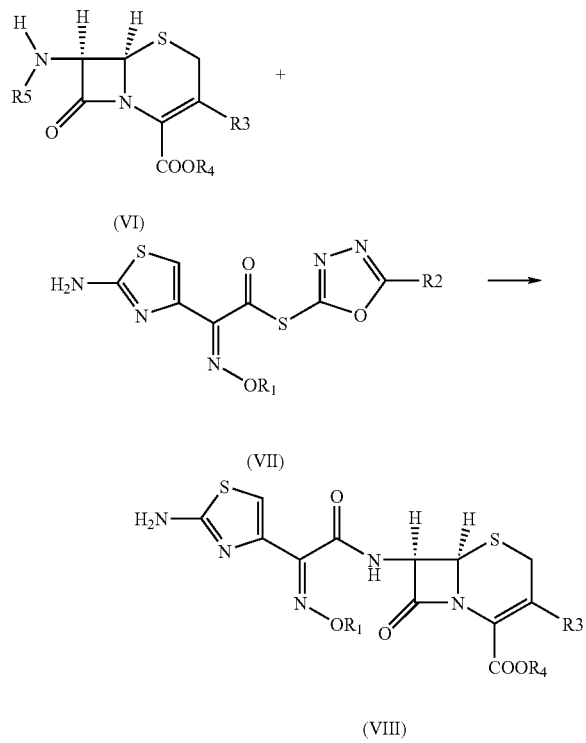

Scheme II (VI)

(VII)

(VIII)

U.S. Pat. No. 6,093,814 discloses a process for the preparation of cefdinir and its intermediate as represented in Scheme III:

In this process p-methoxybenzyl 7-amino-3-vinyl-3-cephem-4-carboxylate is condensed with 2-mercaptobenzothiazolyl (Z)-(2-amino-4-thiazolyl)-2-(trityloxyimino)acetate in N,N-dimethyl acetamide, and the product obtained was treated with p-toluenesulfonic acid in the presence of a mixture of diethyl ether and methanol to get crystalline 7-[(2-amino-4-thiazolyl)-2-(Z)-(trityloxyimino)acetamido]-3-vinyl-3-cephem-4-carboxylic acid.pTSA.2DMAc solvate. This process utilizes highly volatile, low-boiling and therefore industrially-not-preferred solvent, diethyl ether, for crystallizing out the above solvate. In addition, the quantity of the low-boiling solvent used is also very high ranging from 60–100 volumes, thereby adding hazard to the operations. Added to this is the fact that the recovery of these solvents from their mixture is not straight-forward.

U.S. Pat. No. 6,350,869 discloses the purification of impure cefdinir through the preparation of N,N-dicyclohexylamine salt of 7-[2-amino-4-thiazolyl-2-(z)-hydroxyimino acetamido]-3-vinyl-3-cephem-4-carboxylic acid and subsequent hydrolysis to get pure cefdinir. This process requires the preparation of crude cefdinir, conversion to N,N-dicyclohexylamine salt and then hydrolysis of the salt to get pure cefdinir, and therefore the overall yield is not attractive.

U.S. Pat. No. 6,350,869 also emphasizes that cefdinir is unstable in the presence of other amines, with which, it gets heavily degraded. In addition, Yoshihiko Okamoto et al. (J. Pharm. Sci. Vol. 8(9), 976, 1996) report that cefdinir may be unstable under basic environment.

Crystalline cefdinir has limitations in formulation development as it cannot be developed into tablets.

Considering the foregoing limitations, we undertook an investigation in our lab to develop a product which is easy to handle and convenient to develop a dosage which is easily absorbable. We also parallel undertook an investigation to identify a process, which involves (i) less number of steps, Scheme III

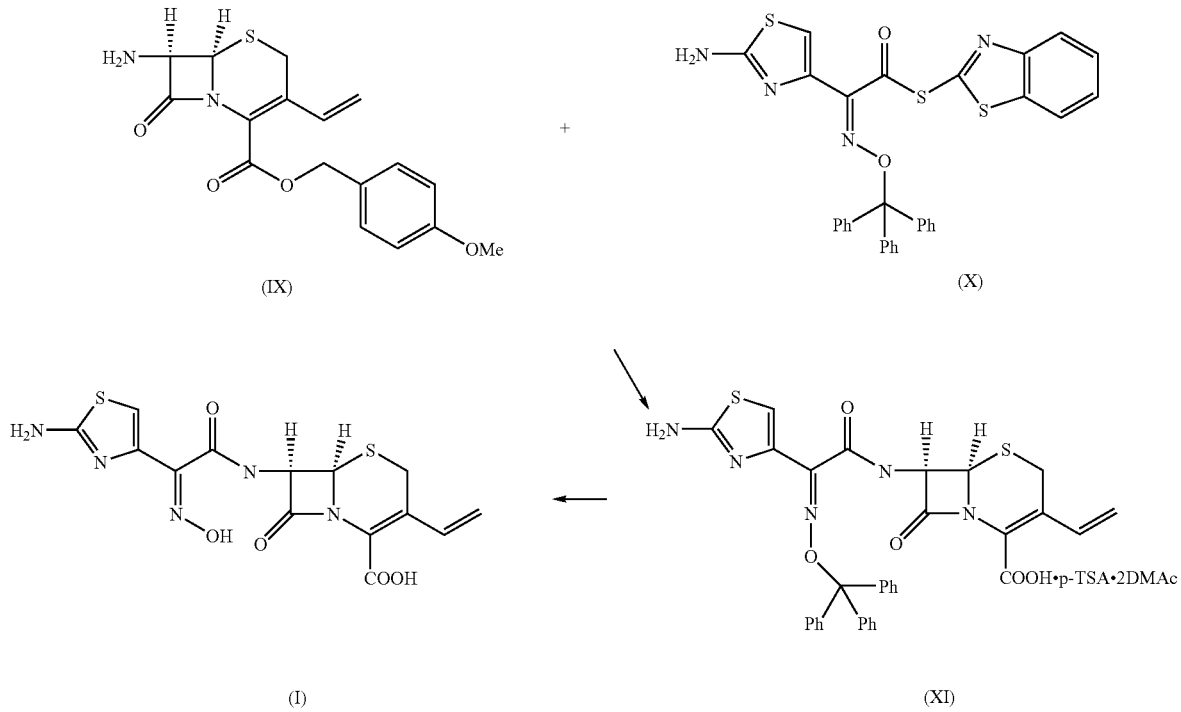

(IX)

(X)

(I)

(XI)

(ii) the direct isolation of cefdinir, with out the need to prepare crude cefdinir in an additional step. This would permit commercializing the production of high-pure cefdinir with industrial-friendly solvent, which can further be recovered for recycling.

OBJECTIVES OF THE INVENTION

The main objective of the present invention is to provide a novel amorphous monohydrate of cefdinir which has very good bioavailability and useful in developing different dosage forms.

Another objective of the present invention is to provide a commercially viable process for the preparation of cefdinir and novel amorphous monohydrate of cefdinir of the formula (I), which would be easy to implement on manufacturing scale.

Yet another objective of the present invention is to provide new salts of formula (XIV), which are insoluble and stable throughout the process of producing the cefdinir and a process for the preparation of cefdinir using these new salts.

SUMMARY OF THE INVENTION

In an embodiment of the present invention, there is provided process for the preparation of cefdinir of the formula (I)

comprising the steps of:
i) condensing 7-amino-3-cephem-4-carboxylic acid of the formula (XII) wherein $R_1$ is as defined above with compound of the formula (XIII) in the presence of a tertiary amine and an organic solvent, followed by treatment with a base to produce a salt of compound formula (XIV), wherein $M^+$ is a counter ion and
ii) hydrolyzing the compound of the formula (XIV) using an acid in the presence of a solvent to produce cefdinir of formula (I).

The reaction is shown in scheme-IV below:

Scheme IV

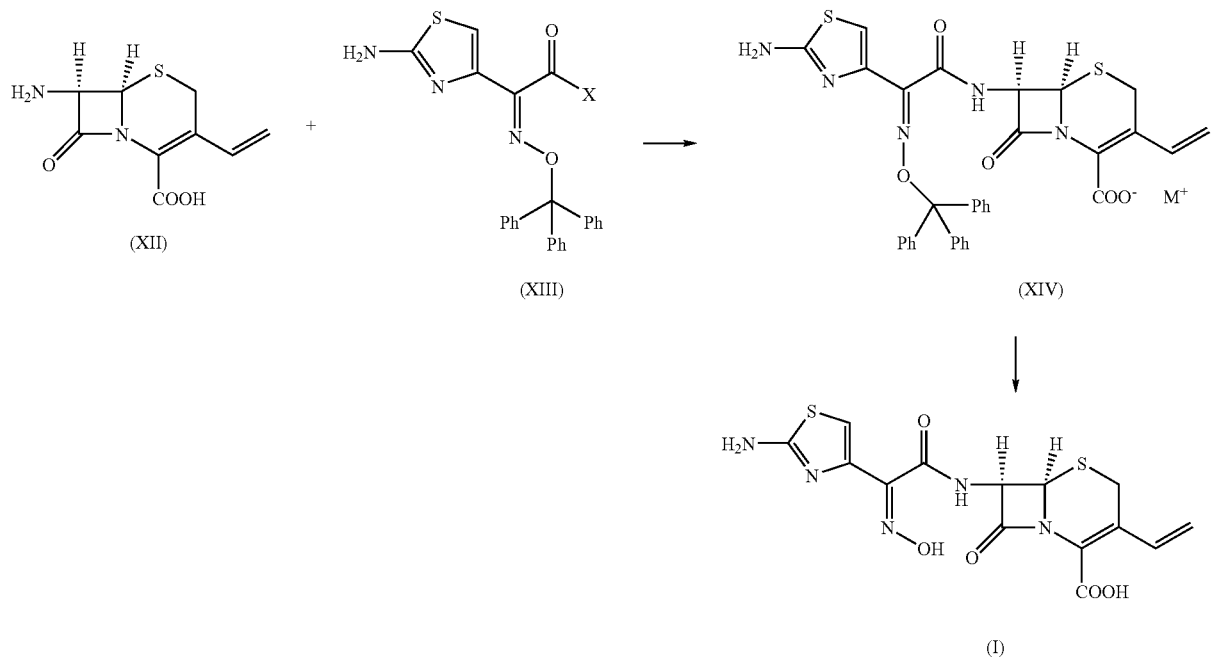

Another embodiment of the present invention provides a novel amorphous monohydrate of cefdinir of the formula (I).

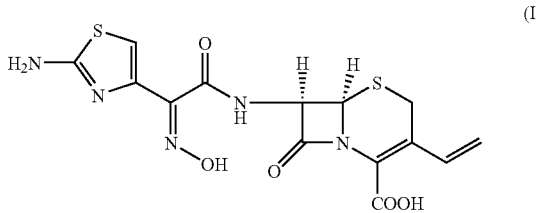

In yet another embodiment of the present invention, there is provided a process for the preparation of novel amorphous monohydrate of cefdinir of the formula (I) comprising hydrolyzing the compound of the formula (XV)

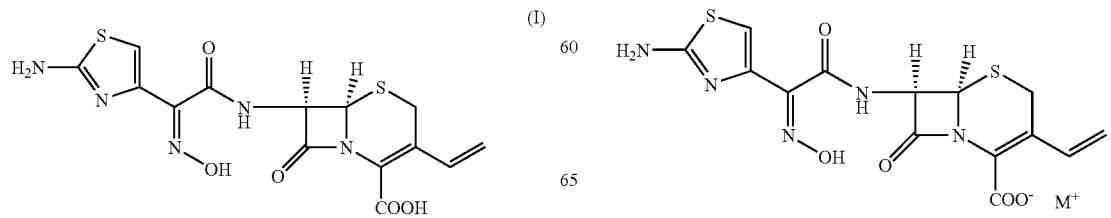

comprising the steps of:
i) adding an organic solvent to compound of formula (XV),
ii) adjusting the pH of the resulting solution using an acid at a temperature in the range of 10 to 40° C.,
iii) cooing the resulting solution rapidly to −40 to 0° and
iv) isolating the novel amorphous monohydrate of cefdinir of the formula (I).

In yet another embodiment of the present invention, there is provided a process for the preparation of novel amorphous monohydrate of cefdinir of the formula (I) comprising hydrolyzing the compound of the formula (XV)

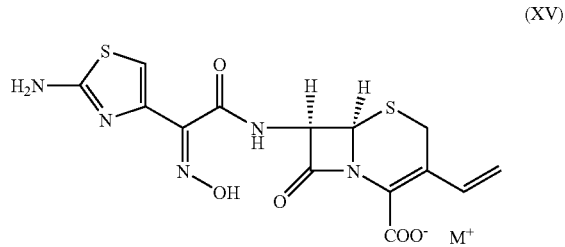

(XV)

comprising the steps of
i) adding an organic solvent to compound of formula (XV),
ii) cooing the resulting solution to −40 to 0° and
iii) adjusting the pH of the resulting solution by rapid addition of an acid at a temperature in the range of 10 to 40° C.,
iv) isolating the novel amorphous monohydrate of cefdinir of the formula (I).

DETAILED DESCRIPTION OF THE INVENTION

Figure 1:
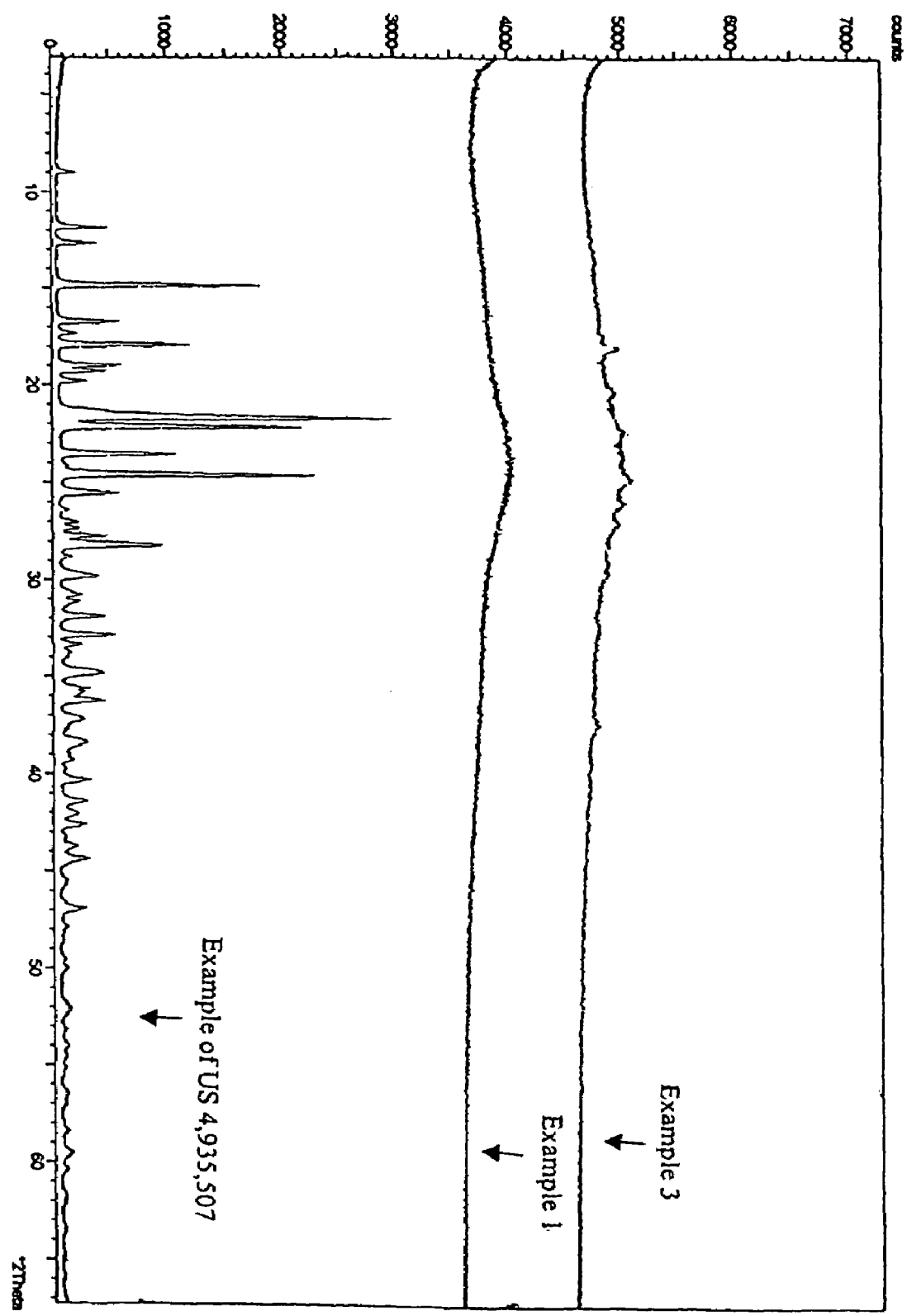
FIG. 1: Comparison of powder XRD pattern of the sample prepared according to U.S. Pat. No. 4,935,507 and the sample prepared according to example 3 and example 4.

In an embodiment of the present invention, the activation group represented by X is selected from ester, thioester, halogen atom such as chlorine, bromine, iodine,

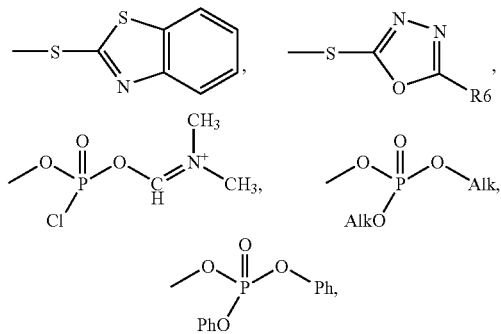

where $R_6$ represents $(C_1-C_4)$alkyl group such as methyl, ethyl, n-propyl, iso-propyl, n-butyl or iso-butyl or a phenyl group; Alk group represents $(C_1-C_4)$alkyl group such as methyl, ethyl, n-propyl, iso-propyl, n-butyl or iso-butyl.

In an other embodiment of the present invention, the counter ion represented by M is selected from sodium, potassium, lithium, magnesium, ammonium, dicyclohexylamine, N,N'-dibenzylethylenediamine, 1,8-diazabicyclo (5.4.0)undec-7-ene (DBU), 1,5-diazabicyclo(4.3.0)non-5-ene, N,N'-diphenylethylenediamine, 1,4-dizabicyclo(2.2.2) octane, N,N-diisopropylethylamine, N,N-diisopropylamine and the like.

In another embodiment of the present invention, the tertiary amine used for condensation in step (i) is selected from triethylamine, N-methylpiperidine, N,N-diisopropylethylamine, trimethylamine and the like.

In yet another embodiment of the present invention, the organic solvent used for condensation in step (i) is selected from ethanol, methanol, isopropanol, THF, cyclohexanol, acetone, butan-2-one, acetonitrile, DMAc, water or a mixture thereof.

In yet another embodiment of the present invention, the base used for condensation in step (i) is selected from sodium hydroxide, sodium acetate, sodium 2-ethyl hexanoate, potassium hydroxide, ammonium hydroxide, ammonium acetate, calcium hydroxide, dicyclohexyl amine, N,N'-dibenzylethylenediamine diacetate, 1,8-diazabicyclo(5.4.0) undec-7-ene (DBU), 1,5-diazabicyclo(4.3.0)non-5-ene, N,N'-diphenylethylenediamine, 1,4-diazabicyclo(2.2.2)octane, N,N-diisopropylethylamine, N,N-diisopropylamine, and the like.

In yet another embodiment of the present invention, the organic solvent used for hydrolysis is selected from acetone, 2-butanone, methanol, isopropanol, ethanol, THF, acetonitrile, DMAc, water and the like or mixtures thereof.

In another embodiment of the present invention, the hydrolysis is carried out using acid selected from HCl, sulfuric acid, formic acid, acetic acid, aromatic/aliphatic sulfonic acids such as benzenesulfonic acid, p-toluenesulfonic acid, naphthalenesulfonic acid, methanesulfonic acid, triflic acid, and the like.

In yet another embodiment of the present invention, the compound of formula (I) obtained is a syn isomer.

The present invention is based on the observation that rapid cooling of the aqueous solvent solution of cefdinir to low temperatures and adding the acid rapidly produces amorphous cefdinir. The technique can be achieved either by cooling the aqueous solvent solution to low temperatures and adding the acid rapidly to adjust the pH to precipitate the amorphous product or adding the acid to adjust the pH and rapidly cooling the resultant solution to precipitate the amorphous product.

In yet another embodiment of the present invention, there is provided new salts of compounds of formula (XIV)

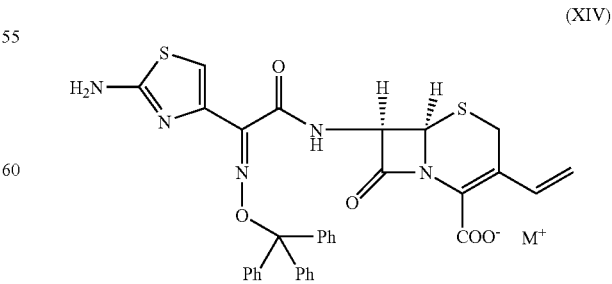

(XIV)

wherein $M^+$ represents a counter ion as defined above.

The foregoing technique has been found to be markedly attractive, both from commercial point of view, as well as from manufacturing viewpoint and affords good quality of amorphous cefdinir of the formula (I).

Many other beneficial results can be obtained by applying disclosed invention in a different manner or by modifying the invention with the scope of disclosure.

The present invention is illustrated with the following examples, which should not be construed as limiting to the scope of the invention.

EXAMPLE 1

Step (i)

Preparation of 2-mercapto-5-phenyl-1,3,4-oxadiazolyl-(Z)-(2-aminothiazol-4-yl)-2-(trityloxyimino) acetate To an ice-cold suspension of (Z)-(2-aminothioazol-4-yl)-2-(trityloxyimino)acetic acid (25 gm) in tetrahydrofuran (200 ml), triethylamine (10 gm) was added dropwise over 10 minutes at 0–5° C. Bis-(2-oxo-oxazolidinyl)phosphinic chloride (15.4 gm) was added and stirred for one hour at 0–5° C. To the reaction mixture 2-mercapto-5-phenyl-1,3,4-oxadiazole (9.8 gm) and triethylamine (5.0 gm) was added dropwise over 15 minutes and stirred at 0–5 ° C. for 6–7 hours. After completion of reaction, chilled water (500 ml) was added at 10–20° C. in 30–40 minutes and stirred at 20° C. for 2 hours. Then the slurry was cooled to 5–10° C. and stirred at this temperature for 45 minutes. The product thus obtained was filtered washed with water (100 ml) and dried at 30–35° C. for 4–5 hours to yield the title compound (50 gm, water content is 40%).

Step (ii)

Preparation of potassium 7β-[2-(2-amino-4-thiazolyl)-2-(Z-trityloxyimino)acetamido]-3-vinyl-3-vinyl-3-cephem-4-carboxylate To a chilled suspension of 7-amino-3-vinyl-3-cephem-4-carboxylic acid (25 gm) and 2-mercapto-5-phenyl-1,3,4-oxadiazolyl-(Z)-(2-aminothiazol-4-yl)-2-(trityloxyimino) acetate (155 gm, water content is 40%) in N,N-dimethylacetamide (150 ml), triethylamine (23 gm) was added drop-wise at 10±2° C. over 30–45 minutes and the resulting mixture was stirred at 20±2° C. for 6–8 hours. The reaction was monitored by HPLC. After completion of the reaction, tetrahydrofuran (125 ml), 10% sodium chloride solution (250 ml) and ethyl acetate (250 ml) were added at 25° C. and stirred for 20 min. The aqueous layer was separated and washed with ethyl acetate (250 ml). To the aqueous layer, ethyl acetate (500 ml) was added, cooled to 10–15° C., and the pH was adjusted to 2.8–3.0 by 1:1 HCl in 30 min. The layers were separated and to the ethylacetate layer, 12% (w/v) methanolic potassium hydroxide solution (60 ml) was added dropwise in 30 min at 25° C., and stirred for 45 min. The resulting slurry was filtered, washed with ethyl acetate (150 ml) followed by acetone (150 ml) and dried at 30–35° C. under vacuum to obtain the title compound (45 gm, HPLC Purity>99.0%).

Step (iii)

Preparation of 7β-[2-(2-amino-4-thiazolyl)-2-(Z-hydroxyimino)acetamido]-3-vinyl-3-cephem-4-carboxylic acid A mixture of potassium 7β-[2-(2-amino-4-thiazolyl)-2-(Z-trityloxyimino)acetamido]-3-vinyl-3-cephem-4-carboxylate (25 gm) and activated carbon (2.5 gm) was added to an aqueous acetone solution (1:1, 70 ml) containing p-toluenesulphonic acid (17.7 gm) at 50° C. The reaction mixture was heated to 70° C. in 20 minutes and maintained at this temperature for 35 minutes. After completion of the reaction, chilled ethylacetate (200 ml) having temperature −15° C. was added to the reaction mixture to reduce the temperature to 30–35° C. The carbon was filtered and the carbon bed was washed with water (50 ml). The filtrate was diluted with water (200 ml), warmed to 35° C. and pH of the solution was adjusted to 6.0–6.5 using aqueous ammonia solution (20%). The aqueous layer was separated and treated with carbon (2.0 gm) at 35° C. for 35 min. The carbon was filtered and the carbon bed was washed with water (50 ml). Acetone (25 ml) was added to the filtrate and 10% (w/v) solution of sulphuric acid was added dropwise to bring down the pH from 4.5 to 2.8 at 33–35° C., stirred for 30 minutes and adjusted the pH again to 2.6. The resulting slurry was stirred for 15–20 minutes at 33–35° C., cooled to 20–25° C., and stirred for 30 minutes. The product thus obtained was filtered, washed with water (50 ml) and dried at 35° C. under vacuum for 3–4 hours to get the title compound (9.0 gm, HPLC purity>99%).

EXAMPLE 2

Step (i)

Preparation of 2-mercapto-5-phenyl-1,3,4-oxadiazolyl-(Z)-(2-aminothiazol-4-yl)-2-(trityloxyimino) acetate To an ice-cold suspension of (Z)-(2-aminothioazol-4-yl)-2-(trityloxyimino)acetic acid (25 gm) in tetrahydrofuran (200 ml), triethylamine (10 gm) was added dropwise over 10 minutes at 0–5° C. Bis-(2-oxo-oxazolidinyl)phosphinic chloride (15.4 gm) was added and stirred for one hour at 0–5° C. To the reaction mixture 2-mercapto-5-phenyl-1,3,4-oxadiazole (9.8 gm) and triethylamine (5.0 gm) was added dropwise over 15 minutes and stirred at 0–5° C. for 6–7 hours. After completion of reaction, chilled water (500 ml) was added at 10–20° C. in 30–40 minutes and stirred at 20° C. for 2 hours. Then the slurry was cooled to 5–10° C. and stirred at this temperature for 45 minutes. The product thus obtained was filtered washed with water (100 ml) and dried at 30–35° C. for 4–5 hours to yield the title compound (50 gm, water content is 40%).

Step (ii)

Preparation of potassium 7β-12-(2-amino-4-thiazolyl)-2-(Z-trityloxyimino)acetamidol-3-vinyl-3-3-vinyl-3-cephem-4-carboxylate To a chilled suspension of 7-amino-3-vinyl-3-cephem-4-carboxylic acid (5 gm) and 2-mercapto-5-phenyl-1,3,4-oxadiazolyl-(Z)-(2-aminothiazol-4-yl)-2-(trityloxyimino)acetate (24.2 gm) in tetrahydrofuran (40 ml) and water (5 ml), triethylamine (4.6 gm) was added drop-wise at 20±2° C.

over 10–15 minutes and the resulting mixture was stirred at 30±2° C. for 6–8 hours. The progress of the reaction was monitored by HPLC. After completion of reaction, ethylacetate (100 ml) and water (75 ml) were added at 30±9° C. and stirred for 20 min. The aqueous layer was separated and washed with ethyl acetate (75 ml). To the aqueous layer, ethylacetate (150 ml) was added, cooled to 10–15° C., and the pH was adjusted to 2.8–3.0 by 1:1 HCl solution in 25–30 min. To the separated ethylacetate layer, acetone (50 ml) and a methanolic potassium hydroxide solution (7.5% w/v, 20 ml) were added dropwise in 25–30 min at 25–27° C. and stirred for further 45 min. The resulting slurry was filtered, washed with acetone (2×25 ml) and dried at 30–35° C. under vacuum to obtain the title compound (5.0 gm, HPLC Purity>99.0%).

Step (iii)

Preparation of 7β-[2-(2-amino-4-thiazolyl)-2-(Z-hydroxyimino)acetamido]-3-vinyl-3-cephem-4-carboxylic acid A mixture of potassium 7β-[2-(2-amino-4-thiazolyl)-2-(Z-trityloxyimino)acetamido]-3-vinyl-3(25 gm) and activated carbon (2.5 gm) was added to an aqueous acetone solution (1:1, 70 ml) containing p-toluenesulphonic acid (17.7 gm) at 50° C. The reaction mixture was heated to 70° C. in 20 minutes and maintained at this temperature for 35 minutes. After completion of the reaction, chilled ethylacetate (200 ml) having temperature −15° C. was added to the reaction mixture to reduce the temperature to 30–35° C. The carbon was filtered and the carbon bed was washed with water (50 ml). The filtrate was diluted with water (200 ml), warmed to 35° C. and pH of the solution was adjusted to 6.0–6.5 using aqueous ammonia solution (20%). The aqueous layer was separated and treated with carbon (2.0 gm) at 35° C. for 35 min. The carbon was filtered and the carbon bed was washed with water (50 ml). Acetone (25 ml) was added to the filtrate and 10% (w/v) solution of sulphuric acid was added dropwise to bring down the pH from 4.5 to 2.8 at 33–35° C., stirred for 30 minutes and adjusted the pH again to 2.6. The resulting slurry was stirred for 15–20 minutes at 33–35° C., cooled to 20–25° C., and stirred for 30 minutes. The crystals thus obtained was filtered, washed with water (50 ml) and dried at 35° C. under vacuum for 3–4 hours to get the title compound (9.0 gm, HPLC purity<99%).

EXAMPLE 3

Preparation of (Z)-7β-[2-(2-amino-4-thiazolyl)-2-(hydroxyimino)acetamido]-3-vinyl-3-cephem-4-carboxylic acid in amorphous hydrate form Ammonium (Z)-7β-[2-(2-amino-4-thiazolyl)-2-(hydroxyimino)acetamido]-3-vinyl-3-cephem-4carboxylate (20 gm) was added to a mixture of water (250 ml) and acetone (80 ml) and warmed to 33–35° C. This aqueous solution was treated with activated charcoal and EDTA at 35° C. for 40 minutes. The carbon was filtered and the carbon bed was washed with water (70 ml). This aqueous acetone solution was cooled to −30° C. and a (10%) solution of aqueous sulphuric acid was added rapidly, stirred for 30 minutes and warmed to 0–2° C. The product thus obtained was filtered at 0–2° C., washed with cold-water (100 ml) and dried at 40–45° C. under vacuum for 5–6 hours to get (Z)-7β-[2-(2-amino-4-thiazolyl)-2-(hydroxyimino)acetamido]-3-vinyl-3-cephem-4-carboxylic acid (6.0 gm, HPLC quality 89.0%, water content 4–5%).

EXAMPLE 4

Preparation of (Z)-7β-[2-(2-amino-4-thiazolyl)-2-(hydroxyimino)acetamido]-3-vinyl-3-cephem-4-carboxylic acid in amorphous hydrate form Ammonium (Z)-7β-[2-(2-amino-4-thiazolyl)-2-(hydroxyimino)acetamido]-3-vinyl-3-cephem-4-carboxylic (20 gm) was added to a mixture of water (250 ml) and acetone (80 ml) and warmed to 33–35° C. This aqueous solution was treated with activated charcoal and EDTA at 35° C. for 40 minutes. The carbon was filtered and the carbon bed was washed with water (70 ml). The pH of this aqueous acetone solution was adjusted to 0.6 at 33–35° C. using a (10%) solution of aqueous sulphuric acid. This solution was cooled rapidly to −10° C. and stirred for 30 minutes. The product thus obtained was filtered at −10° C., washed with cold-water (100 ml) and dried at 40–45° C. under vacuum for 5–6 hours to get (Z)-7β-[2-(2-amino-4-thiazolyl)-2-(hydroxyimino)acetamido]-3-vinyl-3-cephem-4-carboxylic acid (6.0 gm, HPLC quality 93.0%, water content 4–5%).

The invention claimed is:
1. A process for the preparation of cefdinir of the formula

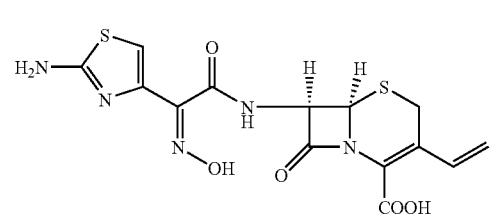

(I)

comprising:
i) condensing 7-amino-3-cephem-4-carboxylic acid of the formula (XII):

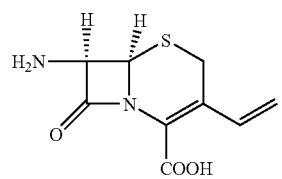

(XII)

wherein $R_1$ is as defined above,
with a compound of the formula (XIII):

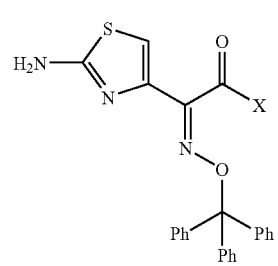

(XIII)

where X represents an activation group,
in the presence of a tertiary amine and a solvent, wherein the solvent is selected from the group consisting of organic solvents and water, followed by treatment with a base to produce a salt of compound formula (XIV):

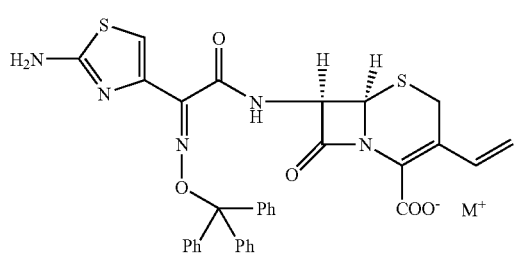

(XIV)

wherein $M^+$ is a counter ion; and ii) hydrolyzing the compound of the formula (XIV) using an acid in the presence of a solvent to produce cefdinir of formula (I).

2. The process according to claim 1, wherein X is selected from the group consisting of a chlorine atom, a bromine atom,

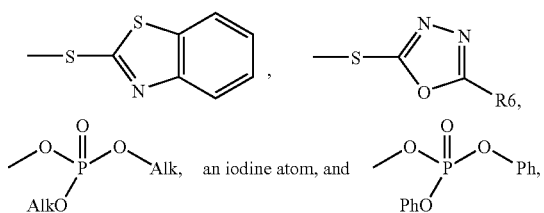

where R6 represents a (C1–C4)alkyl group or a phenyl group and Alk represents a (C1–C4) alkyl.

3. The process according to claim 1, wherein the counter ion represented by M is selected from the group consisting of sodium, potassium, lithium, magnesium, ammonium, dicyclohexylanimonium, N,N-diisopropylethylammonium, and N,N-diisopropylammomum.

4. The process according to claim 1, wherein the tertiary amine is selected from the group consisting of triethylamine, N-methylpiperidine, N,N-diisopropylethylamine, and trimethylamine.

5. The process according to claim 1, wherein the solvent used in step (i) is selected from the group consisting of ethanol, methanol, isopropanol, THF, cyclohexanol, acetone, butan-2-one, acetonitrile, DMAc, water, and mixtures thereof.

6. The process according to claim 1, wherein the solvent used in step (ii) is selected from the group consisting of acetone, 2-butanone, methanol, isopropanol, ethanol, THF, acetonitrile, DMAc, water, and mixtures thereof.

7. The process according to claim 1, wherein the acid is selected from the group consisting of HCl, sulfuric acid, formic acid, acetic acid, and aromatic/aliphatic sulfonic acids.

8. The process according to claim 1, wherein the compound of formula (I) obtained is a syn isomer.

9. A process for the preparation of a novel amorphous monohydrate of cefdinir represented by formula (I):

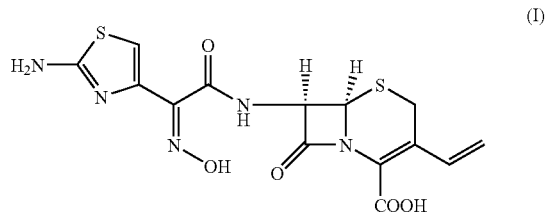

(I)

comprising:
hydrolyzing the compound represented by formula (XV):

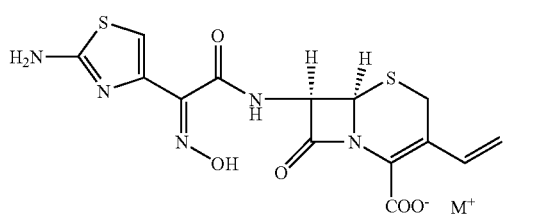

(XV)

wherein $M^+$ represents a counter ion, comprising the steps of:
i) adding a solvent to a compound of formula (XV), wherein the solvent is selected from the group consisting of organic solvents and water,
ii) adjusting the pH of the resulting solution using an acid at a temperature in the range of 10 to 40° C.,
iii) cooling the resulting solution rapidly to −40 to 0° C., and
iv) isolating the novel amorphous monohydrate of cefdinir represented by formula (I).

10. A process for the preparation of novel amorphous monohydrate of cefdinir represented by formula (I):

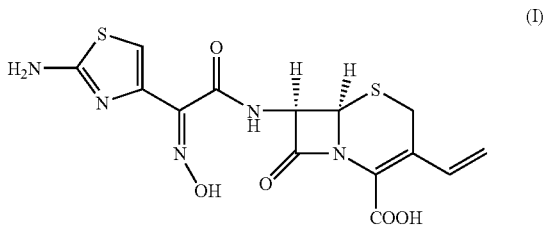

(I)

comprising:
hydrolyzing the compound represented by formula (XV)

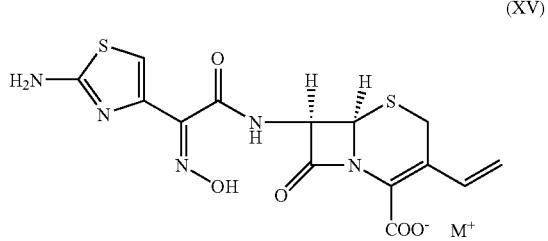

(XV)

comprising the steps of:
i) adding a solvent to a compound of formula (XV), wherein the solvent is selected from the group consisting of organic solvents and water,
ii) cooling the resulting solution to −40 to 0°C. and
iii) adjusting the pH of the resulting solution by rapid addition of an acid at a temperature in the range of 10 to 40°C., and
iv) isolating the novel amorphous monohydrate of cefdinir represented by formula (I).

11. The process according to claim 9, wherein the solvent is selected from the group consisting of acetone, 2-butanone, methanol, isopropanol, ethanol, THF, acetonitrile, DMAc, water and mixtures thereof.

12. The process according to claim 9, wherein the acid is selected from the group consisting of HCl, sulfuric acid, formic acid, acetic acid, and aromatic/aliphatic sulfonic acids.

13. A compound of compound formula (XIV),

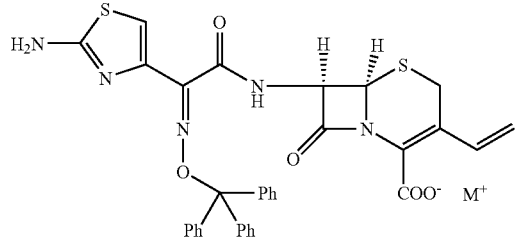

(XIV)

wherein M$^+$ represents a counter sodium ion or potassium ion.

* * * * *